US010166136B2

(12) United States Patent
Poucher

(10) Patent No.: US 10,166,136 B2
(45) Date of Patent: *Jan. 1, 2019

(54) METHOD OF IMPLANTING A PENILE PROSTHETIC

(71) Applicant: Coloplast A/S, Humlebaek (DK)

(72) Inventor: Neal Poucher, North Oaks, MN (US)

(73) Assignee: Coloplast A/S, Humlebaek (DK)

( * ) Notice: Subject to any disclaimer, the term of this patent is extended or adjusted under 35 U.S.C. 154(b) by 154 days.

This patent is subject to a terminal disclaimer.

(21) Appl. No.: 15/281,079

(22) Filed: Sep. 30, 2016

(65) Prior Publication Data

US 2017/0014260 A1 Jan. 19, 2017

Related U.S. Application Data

(63) Continuation of application No. 14/454,733, filed on Aug. 8, 2014, now Pat. No. 9,480,566.

(51) Int. Cl.
*A61F 5/00* (2006.01)
*A61F 5/41* (2006.01)
*A61B 17/00* (2006.01)
*A61F 2/26* (2006.01)

(52) U.S. Cl.
CPC .............. *A61F 5/41* (2013.01); *A61B 17/00* (2013.01); *A61F 2/26* (2013.01); *A61F 2005/411* (2013.01); *A61F 2005/415* (2013.01)

(58) Field of Classification Search
CPC ..................................... A61F 2/26; A61F 5/41
USPC ...................................................... 600/38–41
See application file for complete search history.

(56) References Cited

U.S. PATENT DOCUMENTS

| 4,049,002 | A | 9/1977 | Kletschka et al. |
| 4,919,152 | A | 4/1990 | Ger |
| 9,480,566 | B2 * | 11/2016 | Poucher ............... A61F 5/41 |
| 9,642,707 | B2 | 5/2017 | Daniel |
| 2001/0005787 | A1 | 6/2001 | Oz et al. |

OTHER PUBLICATIONS

Office Action dated Apr. 5, 2018 in U.S. Appl. No. 15/456,603.
Office Action dated Jan. 3, 2017 in U.S. Appl. No. 14/482,640.

* cited by examiner

*Primary Examiner* — John Lacyk
(74) *Attorney, Agent, or Firm* — Coloplast Corp., Coloplast A/S; Nick Baumann

(57) ABSTRACT

A method of implanting a penile prosthetic includes providing a tool having a barrel with a first groove formed in an exterior surface of the barrel and a second groove formed in the exterior surface of the barrel; capturing opposing lateral edges of a deflated penile implant into the respective first groove the second groove; placing the barrel of the tool and the deflated penile implant into a corpora cavernosum of a penis; removing the barrel from the corpora cavernosum of the penis and leaving the deflated penile implant in the corpora cavernosum of the penis.

13 Claims, 8 Drawing Sheets

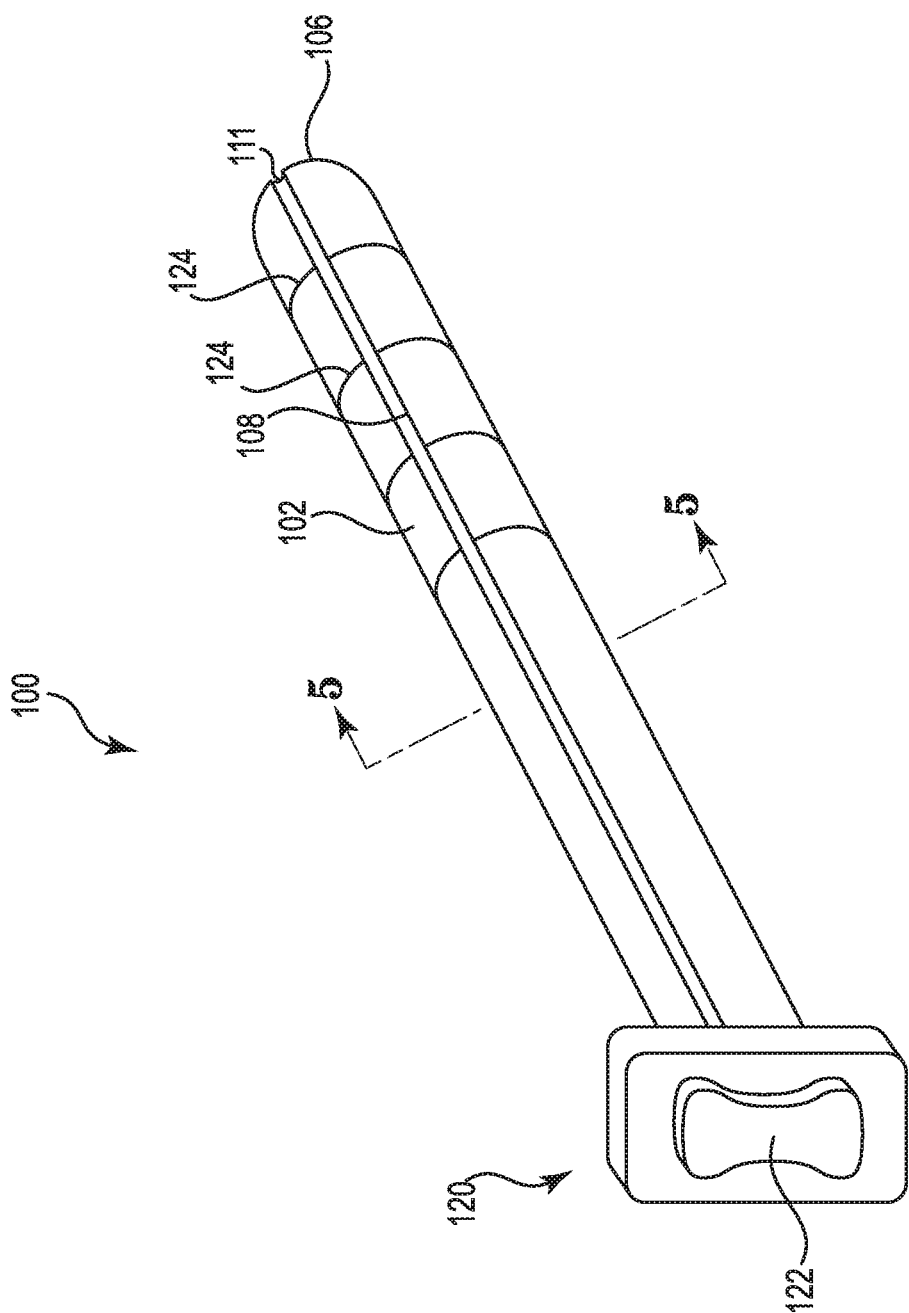

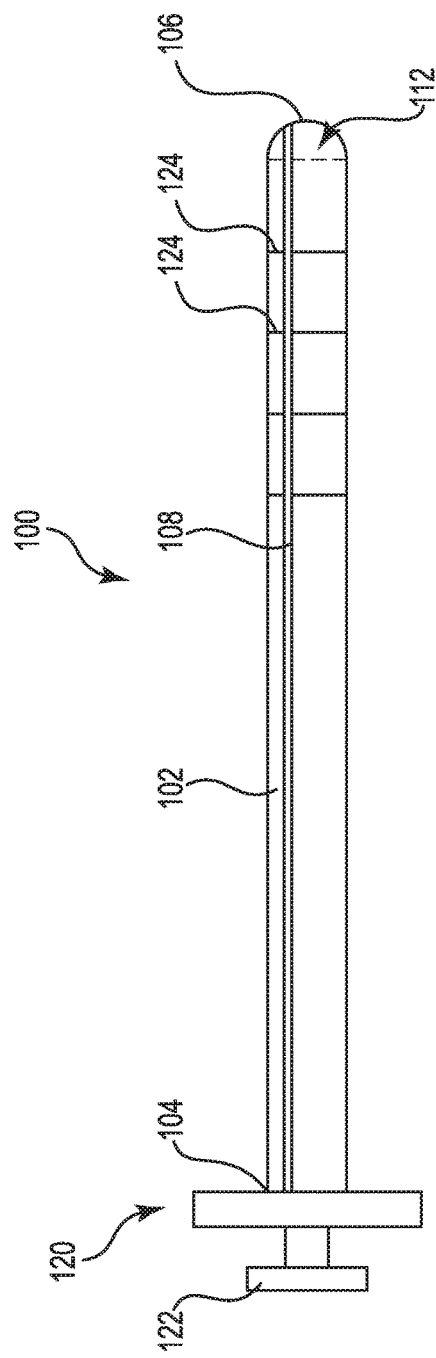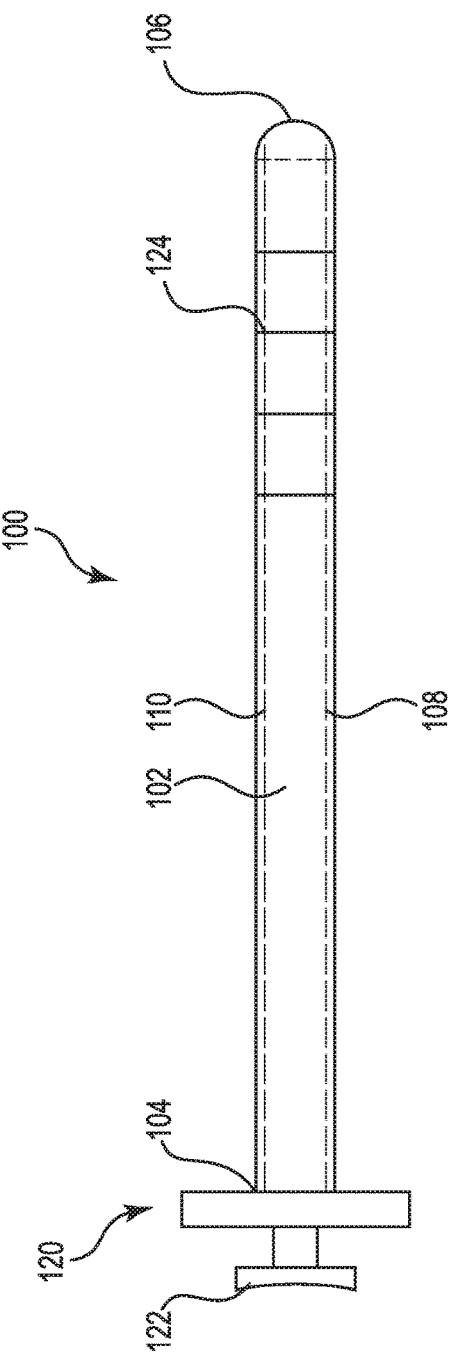

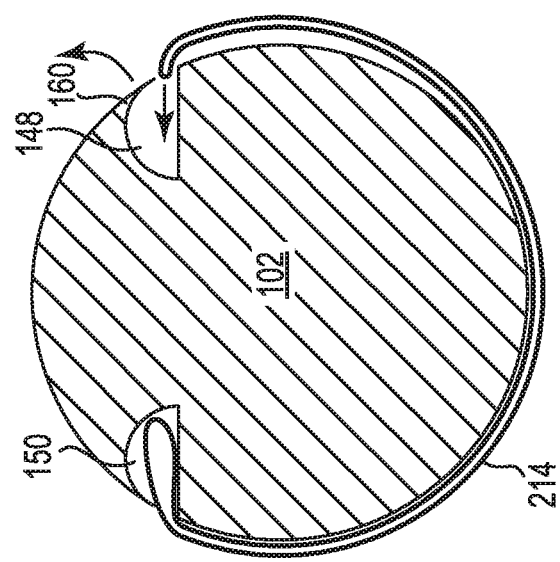

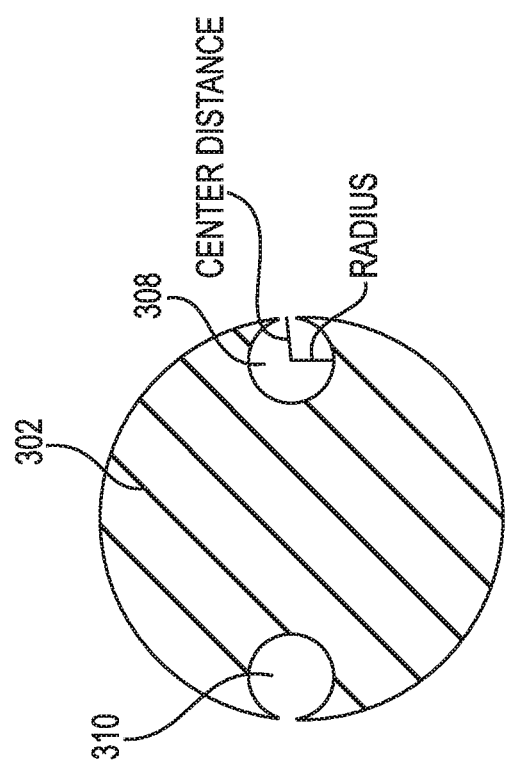

METHOD OF IMPLANTING A PENILE PROSTHETIC

BACKGROUND

An implanted penile prosthetic has proven useful in treating erectile dysfunction in men. The penile prosthetic includes two inflatable cylinders implanted in the penis, a pump implanted in the scrotum or other internal space, and a liquid holding reservoir implanted in the abdomen or other internal space.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (e.g., a "Furlow" introducer) is inserted into each dilated corpora cavernosum to measure a length of the penis distally and proximally to determine a desired length of the cylinders. A cylinder of the appropriately selected length is secured to a suture, and the suture is secured to a needle (sometimes called a "Keith" needle) that is loaded into the Furlow introducer. The Furlow introducer delivers the needle through the dilated corpora cavernosum and out the glans penis. The needle is discarded and the suture is employed to tow the cylinder into place within the dilated corpora cavernosum.

The above-described procedure has proven effective when implanting penile prostheses. However, surgeons and users would both appreciate improved tools for implanting penile prosthetic cylinders.

SUMMARY

One aspect provides a tool for implanting an inflatable penile prosthetic cylinder. The tool includes a barrel having a solid central portion and two groove formed in an exterior side surface of the barrel. The first groove and the second groove each form a cavity extending into the exterior side surface of the barrel toward the solid central portion, and the cavity has a first gap dimension measured at the exterior side surface that is smaller than a second gap dimension measured inboard relative to the exterior side surface of the barrel.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a perspective view of one embodiment of a tool for implanting an inflatable penile prosthetic cylinder.

FIG. 3 is a side view and FIG. 4 is a top view of the tool illustrated in FIG. 2.

FIG. 8 is an end view of a deflated prosthetic cylinder coupled to the tool illustrated in FIG. 2.

FIG. 9 is a cross-sectional view of one embodiment of a tool for implanting an inflatable penile prosthetic cylinder.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

End means endmost. A distal end is the furthest endmost location of a distal portion of a thing being described, whereas a proximal end is the nearest endmost location of a proximal portion of the thing being described. The portion next to or adjacent to an end is an end portion.

The term "hemisphere" in this application means one equatorial half of a sphere.

An implantable penile prosthetic system includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Figures 1A, 1B:
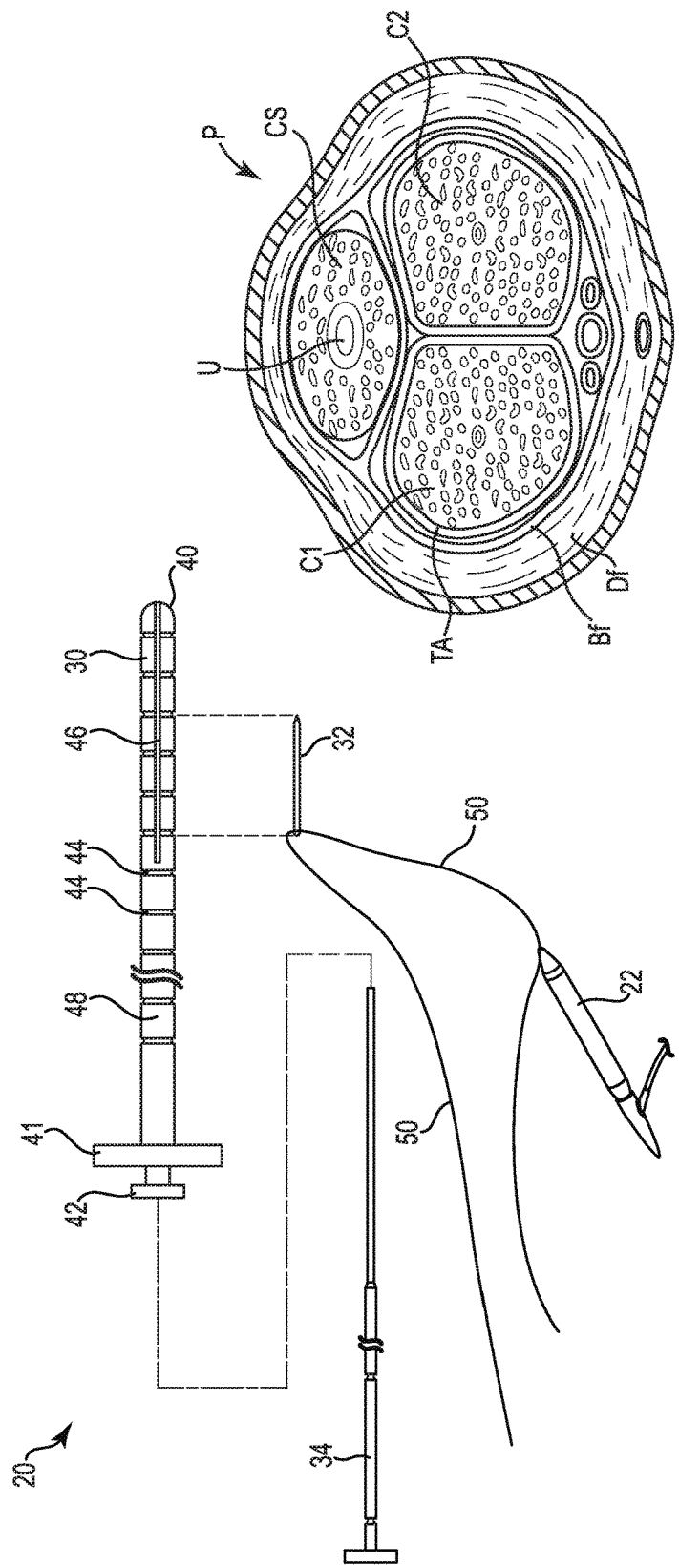
FIG. 1A is an exploded side view of a prior art tool for implanting a cylinder into a penis as illustrated in cross-section in FIG. 1B.

FIG. 1A is an exploded side view of a prior art tool 20 for implanting an inflatable cylinder 22 into a penis P illustrated in FIG. 1B. The inflatable cylinders 22 are fabricated to be pliant and comfortable when deflated and rigid and erect when inflated. The deflated cylinder 22 lacks column strength and will bend and twist and resist being pushed into the penis P. For this reason, a suture or strand is employed to pull the inflatable cylinder into place within the penis P.

The tool 20 includes a barrel 30, a needle 32 that is insertable into the barrel 30, and a plunger 34 that is insertable into the barrel 30 to push the needle 32 out of the barrel 30. One such needle 32 is a Keith needle.

The barrel 30 extends between a curved distal end 40 and a handle 41 provided at a proximal end 42. The barrel 30 has markings 44 applied on an external surface to indicate or measure a depth to which the barrel 30 has been inserted into the corpora cavernosum. The barrel 30 is provided with a slot 46 that is sized to receive the needle 32 and a lumen 48 sized to receive the needle 32 and the plunger 34.

The needle 32 is attached to a tow suture 50 that is coupled with the cylinder 22. The tow suture 50 is generally inserted through an eyelet of the needle 50 and a hole provided at a distal end of the cylinder 22.

The plunger 34 is insertable into the lumen 48 at the proximal end 42 of the barrel 30 and operates to push the needle 32 out of the lumen 48.

FIG. 1B is a cross-sectional view of the penis P oriented to access by the surgeon. The surgeon gains access to the corpora cavernosa though small incisions made through the fascia after the penis is reclined toward the abdomen, as illustrated in the cross-sectional view of FIG. 1B. In the view of FIG. 1B the penis P of the patient is reclined against the torso such that the urethra U, surrounded by corpus spongiosum CS tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated with an appropriate dilation tool to form a recess in the penis P that is sized to receive one of the two cylinders 22. The barrel 30 of the tool 20 is inserted into each dilated corpora cavernosum C1, C2 to measure the length of the corpora prior to selecting an appropriately sized cylinder 22. The barrel 30 is removed from the penis P. The suture 50 is inserted through the distal, leading end of the cylinder 22 and the needle 32. The needle 32 is loaded into the barrel 30 through the slot 46 and the plunger 34 is inserted into the lumen 48 via the proximal end 42 of the barrel 30. The barrel 30 is inserted into the dilated corpora cavernosum and the plunger 34 is pushed into the lumen 48 to push the needle 32 out of the barrel 30 and through the glans penis. The surgeon captures the needle 32, disengages the needle 32 from the tow suture 50, and pulls on the tow suture 50 to draw the cylinder 22 into the dilated corpora cavernosum. The tow suture 50 is disengaged from the cylinder, which is now implanted within the corpora cavernosum C1 or C2.

Pushing the needle 32 through the glans penis can cause bleeding from the head of the penis, which while harmless, can be alarming to the patient. Surgeons have expressed a desire to avoid the use of the needle 32.

As noted above, the suture 50 is inserted through the distal, leading end of the cylinder 22. The distal end of the cylinder 22 is oftentimes structurally reinforced to accommodate the hole that the suture 50 is passed through. The reinforced end of the cylinder can be felt by some patients who perceive it as a hard and unnatural, undesirable pointed projection.

Embodiments provide a tool for implanting a prosthetic cylinder of such a system into a penis, where the tool does away with the handling and the use of a Keith needle. The tool is useful for measuring the depth of the corpora cavernosum in selecting a length of an appropriately sized cylinder, and then can be used to push the deflated prosthetic cylinder into the opening formed in the penis. The tool may be fabricated from plastic or metal and can be provided in both disposable and reusable forms.

FIG. 2 is a perspective view, FIG. 3 is a side view, and FIG. 4 is a top view of one embodiment of a tool 100 useful for implanting an inflatable penile prosthetic cylinder.

The tool 100, as described below, includes a barrel having a solid central portion and a groove formed in an exterior side surface of the barrel between a first convex curved exterior surface and a second convex curved exterior surface of the barrel. The groove extends to and forms an opening at a distal end of the barrel and forms a cavity extending into the barrel from the exterior side surface toward the solid central portion. The cavity has a first gap dimension measured at the exterior side surface that is smaller than a second gap dimension measured inboard relative to the exterior side surface of the barrel. The cavity is dimensioned and configured to capture an edge portion of an implantable cylinder after the cylinder is wrapped around the barrel.

In one embodiment, the barrel is provided with one groove (e.g., groove 108) forming one cavity, and the edges of the flattened cylinder are captured in the one cavity.

In one embodiment, the barrel is provided with a second groove (e.g., groove 110) formed in a second exterior side of the barrel between the first convex curved exterior surface and the second convex curved exterior surface, and both of the first groove 108 and the second groove 110 each form a cavity extending into the barrel from an exterior side surface of the barrel toward the solid central portion, and each cavity has a first gap dimension measured at the exterior side surface that is smaller than a second gap dimension measured inboard relative to the exterior side surface of the barrel.

In one embodiment, the tool 100 includes a barrel 102 extending between a proximal end 104 and a distal end 106, with a pair of grooves 108, 110 that extend to the distal end 106 of the barrel 102. The first groove 108 and the second groove 110 extend all the way to and form an opening 111 in the distal end 106 of the barrel 102. The grooves 108, 110 form cavities longitudinally within the barrel 102, where each cavity is sized to receive a deflated edge of the prosthetic cylinder and each groove operates to clamp down on a portion of the deflated prosthetic cylinder.

In one embodiment, the first groove 108 and the second groove 110 extend from the proximal end 104 to the distal end 106 of the barrel 102. The distal end 106 of the barrel 102 is formed to be a blunt end that is sized to fit into the glans penis when inserting the deflated prosthetic cylinder. One example of a blunt distal end 106 of the barrel 102 is a hemispherical end 112. The length of the barrel 102 between the proximal end 104 and the distal end 106 is selected based on the length of the penis (distal from the incision or access area formed in the penis) and the length of the prosthetic cylinder. Suitable lengths for the barrel 102 are in a range from 10 cm to 20 cm, with one length of a prosthetic cylinder implant being about 16 cm.

In one embodiment, a handle 120 is attached to the proximal end 104 of the barrel 102. The handle 120 allows the surgeon to grasp the barrel 102 and apply pressure in the distal direction when inserting the prosthetic cylinder. One example of the handle 120 includes a push pad 122 (or a pad 122) that has a concave curve sized to receive pressure from the surgeon's thumb when manipulating the tool 100.

Embodiments provide demarcations or markings 124 similar to a ruler, where the markings 124 are useful in measuring the depth that the barrel 102 is inserted into the penis. The markings 124 assist in selecting a prosthetic cylinder with an appropriate length for the patient. The markings 124 include printed indicia or indicia engraved into a surface of the barrel.

Figure 5:
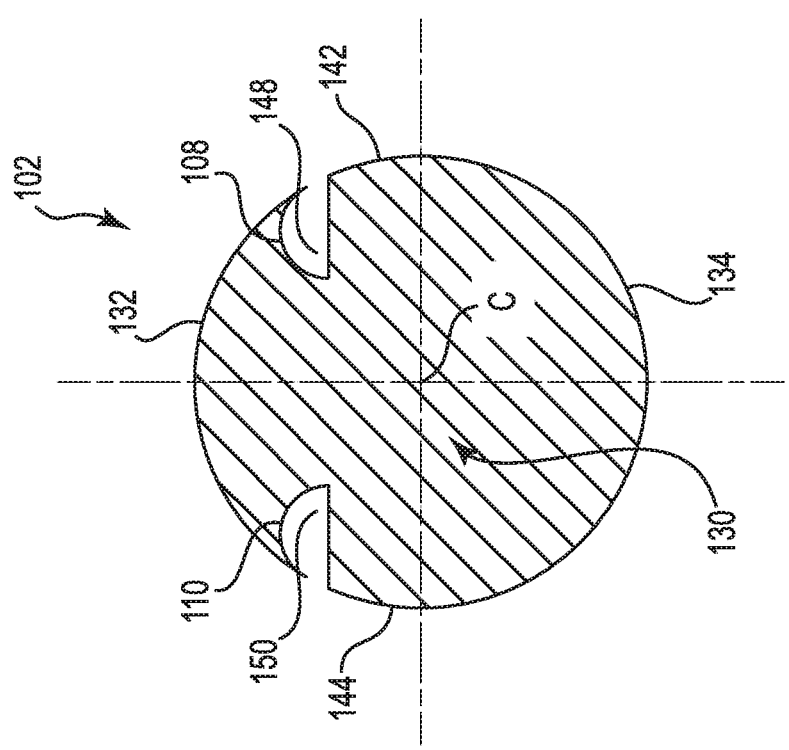
FIG. 5 and FIG. 6 are cross-sectional views of a barrel of the tool illustrated in FIG. 2.

FIG. 5 is a cross-sectional view of the barrel 102. The barrel 102 has a solid central portion 130 surrounding its geometric center C. In one embodiment, the barrel 102 is substantially circular in lateral cross-section. Other shapes for the cross-section of the barrel 102 other than circular are also acceptable. For example, cross-sectional shapes such as an elongated oval or segments of a circle connected by straight lines (edges) are also acceptable.

The central portion 130 is bounded by a first convex curved exterior surface 132 opposite from a second convex curved exterior surface 134, and is located between a first exterior side surface 142 and a second exterior side surface 144. The grooves 108, 110 are generally formed in the exterior side surfaces 142, 144, respectively, and extend into the barrel 102 from each exterior side surface toward the solid central portion 130. The grooves 108, 110 extend to the end of the barrel 102 to form a pair of openings in the distal end 106. Each of the grooves 108, 110 forms a cavity 148, 150 in one of the exterior side surfaces 142, 144, respectively, between the first 132 and the second 134 curved exterior surfaces.

Figure 6:
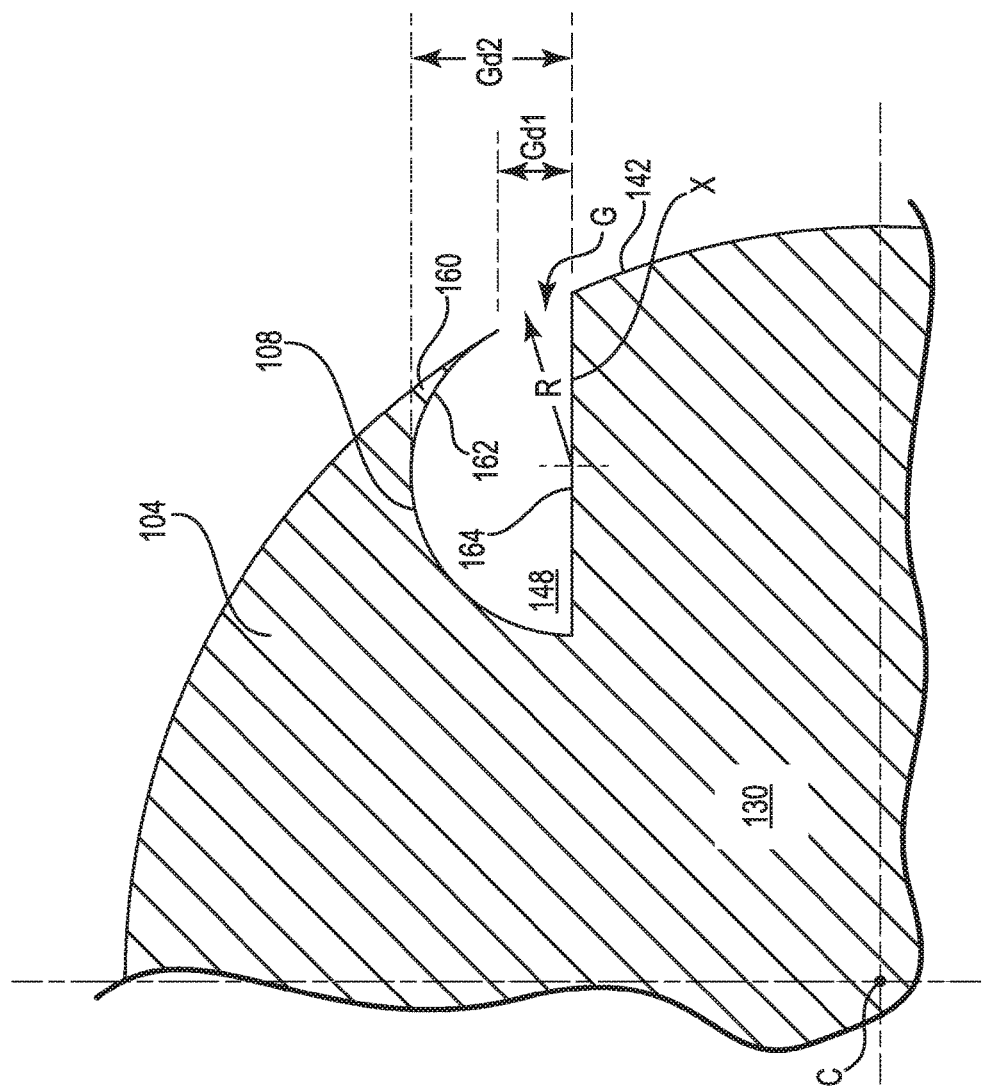

FIG. 6 is a cross-sectional view of the cavity 148. Each of the cavities is formed as a slot that extends a length along the barrel 102. The cavity 148 is formed in the exterior side surface 142 at a center that is a distance X away from the exterior side surface 142. The center of the cavity 148 or the slot 148 is located such that a longitudinal axis through its center is parallel to a longitudinal axis through the center C of the barrel 102. The cavity 148 or the slot 148 is formed with a radius R that is larger than the distance X, which results in a gap G being formed in the exterior side surface 142.

In one embodiment, the barrel 102 is substantially circular and has an exterior perimeter formed by the side surfaces 142, 144. Each of the cavities 148, 150 is formed as a slot that creates an opening in the exterior perimeter (or side surface 142) of the barrel 102. Each slot, for example slot 148, has a slot center X that is parallel in the longitudinal sense with the center C of the barrel 102, and a radius of the slot 148 is larger than the distance that the slot center X is located away from the exterior perimeter 142. This manner of fabricating the slots 148, 150 provides each slot with a gap or an opening into the cavity.

The cavity 148 is formed to include a gap G at the exterior side surface 142. The cavity 148 has a first gap distance Gd1 measured at the exterior side surface 142 that is less than a second gap distance Gd2 that is measured inboard relative to the exterior side surface 142.

The gap G forms a lip 160. The lip 160 is formed by a remaining portion of the second side surface 142 of the barrel 102 between a first wall 162 and a second wall 164 of the cavity 148. A distance between the lip 160 and a second wall 164 forms the gap G, or specifically, the gap distance Gd1. In one embodiment, the lip 160 is flexible and pre-stressed to provide a clamping force into the direction of the cavity 148. The lip 160 is flexible, and can be lifted outward in a radial direction to allow a portion of the prosthetic cylinder to be inserted into the cavity 148. The lip 160 is configured to recover and provide a clamping force that holds the prosthetic cylinder in the cavity 148.

The tool 100 is employed to deliver a deflated prosthetic cylinder into a dilated corpora cavernosum. The prosthetic cylinder has a wall thickness of about 0.020 inches, such that the deflated cylinder has a thickness of twice the wall thickness, or about 0.040 inches. The cavities 148, 150 are sized to receive the deflated wall thicknesses of the cylinder, and the lip 160 and the gap distance Gd1 are selected to provide a clamping forced against the walls of the deflated cylinders. The gap distance Gd1 is thus less than about 0.040 inches.

Figure 7:
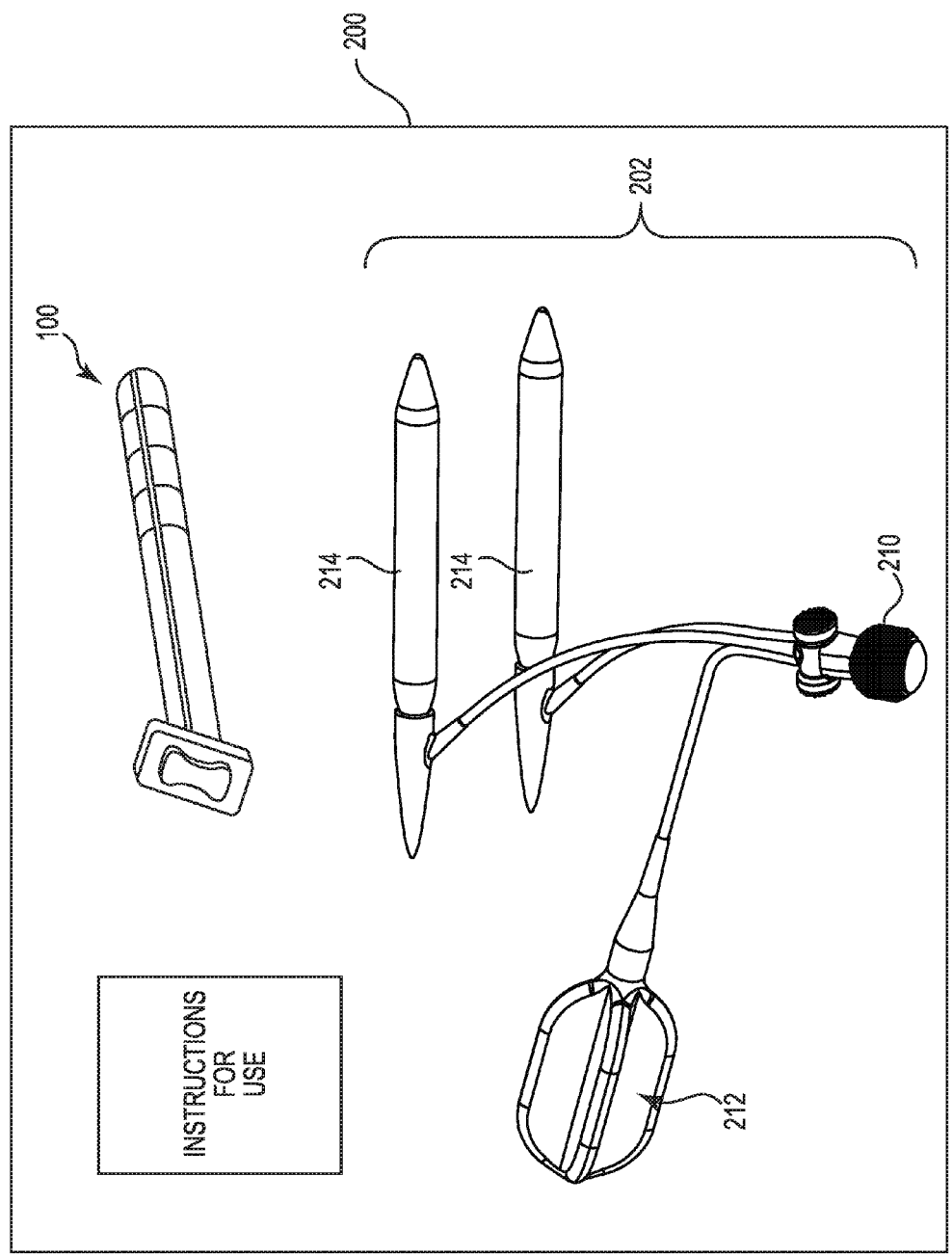
FIG. 7 is a perspective view of a kit of parts including an implantable penile prosthetic system and the tool illustrated in FIG. 2.

FIG. 7 is a schematic view of a kit of parts 200. The kit of parts includes the tool 100, an implantable penile prosthetic system 202, and instructions for use of the tool 100. The implantable penile prosthetic system 202 includes a pump 210 connectable between a reservoir 212 and prosthetic cylinders 214. The pump 210 operates to move liquid from the reservoir 212 and into the inflatable cylinders 214. The inflated cylinders 214, when implanted, provide the penis with an erection. The inflatable cylinders 214 can be deflated by evacuating the air and the liquid from the cylinders, which collapses the cylinders 214 into a flat, pancake shape.

FIG. 8 is a cross-sectional view of one of the deflated cylinders 214 secured to the barrel 102. The view of FIG. 8 is side-to-side relative to the cylinder 214.

The deflated cylinder 214 extends between a first deflated edge that is inserted and retained within the first cavity 150 and a second deflated edge that can be inserted into the cavity 148. The lip 160 is flexible and can be maneuvered upward and out of the way to allow the edge of the cylinder 214 to be inserted into the cavity 148. When the lip 160 is released it provides a clamping force directed into the barrel against the edge of the cylinder 214. With the deflated cylinder 214 secured between the cavities 148, 150 the surgeon inserts the barrel 102 into the opened space formed in one of the corpora cavernosum. The deflated cylinder 214 is delivered through the corpora cavernosum up to the glans penis at which point the surgeon slides the barrel 102 away from the inserted cylinder 214. The deflated cylinder 214 slides out of the cavities 148, 150 and is implanted into the penis.

FIG. 9 is a cross-sectional view of one embodiment of a barrel of a tool that is useful for implanting an inflatable penile prosthetic cylinder into a penis. The barrel 302 includes two cavities 308, 310 (or slots 308, 310) formed by a pair of grooves. In one embodiment, the first groove 308 is located diametrically opposite from the second groove 310. In one embodiment, the first groove 308 is formed as a circular cavity in the barrel 302. The circular cavity 308 is formed on a center parallel to a center of the barrel 302. The center of the cavity is located a center distance away from exterior perimeter of the barrel 302. The center distance of the circular cavity 308 is less than a radius R of the circular cavity 308, which results in the circular cavity 308 forming an opening in the exterior surface of the barrel 302.

Embodiments provide an improved tool for implanting a prosthetic cylinder of an implantable device useful for treating erectile dysfunction. The tool described in this application obviates the use of a Keith needle and does away with perforating the glans penis when implanting a prosthetic cylinder.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method of implanting a penile prosthetic, the method comprising:
   providing a tool having a barrel extending from a proximal end to a distal end, with the barrel having a first groove formed in an exterior surface of the barrel and a second groove formed in the exterior surface of the barrel and located apart from the first groove, with the first groove and the second groove extending to and forming an opening at the distal end of the barrel;
   deflating an inflatable penile implant to provide a deflated penile implant;
   inserting a first lateral edge of the deflated penile implant into the first groove and inserting a second lateral edge of the deflated penile implant into the second groove;
   placing the barrel of the tool and the deflated penile implant into a corpora cavernosum of a penis;
   sliding the barrel of the tool relative to the deflated penile implant, removing the barrel from the corpora cavernosum of the penis, and leaving the deflated penile implant in the corpora cavernosum of the penis.

2. The method of claim 1, further comprising:
   opening a first flexible lip associated with the first groove and inserting the first lateral edge of the deflated penile implant into the first groove; and
   opening a second flexible lip associated with the second groove and inserting the second lateral edge of the deflated penile implant into the second groove.

3. The method of claim 1, further comprising:
   clamping a first flexible lip associated with the first groove against the first lateral edge of the deflated penile implant; and
   clamping a second flexible lip associated with the second groove against the second lateral edge of the deflated penile implant.

4. The method of claim 1, further comprising:
   providing the tool having the first groove formed in the exterior surface of the barrel and the second groove formed in the exterior surface of the barrel at a location diametrically opposite from the first groove; and
   inserting the first lateral edge of the deflated penile implant into the first groove and inserting the second lateral edge of the deflated penile implant into the second groove.

5. The method of claim 1, further comprising:
   dilating the corpora cavernosum of the penis with a dilation tool thus forming a dilated corpora cavernosum of the penis; and
   directing the barrel of the tool and the deflated penile implant into the dilated corpora cavernosum of the penis.

6. The method of claim 1, further comprising:
   pushing against a push pad attached to the proximal end of the barrel and moving the barrel of the tool and the deflated penile implant into the corpora cavernosum of the penis.

7. The method of claim 1, further comprising:
   pushing the barrel of the tool into the corpora cavernosum of the penis and reading a demarcation located on the barrel and measuring a distal length of the corpora cavernosum of the penis.

8. The method of claim 1, further comprising:
   pushing the barrel of the tool into the penis and reading a demarcation located on the barrel and measuring a proximal length of the penis.

9. The method of claim 1, further comprising:
   evacuating air form the inflatable penile implant to provide the deflated penile implant.

10. The method of claim 1, further comprising:
    evacuating air and liquid form the inflatable penile implant to provide the deflated penile implant.

11. The method of claim 1, further comprising:
    implanting a pump into a scrotum;
    implanting a reservoir into an abdomen;
    coupling the pump to the reservoir and to the inflatable penile implant; and
    pumping the pump and inflating the inflatable penile implant.

12. A method of implanting a penile prosthetic, the method comprising:
    providing a tool having a barrel extending from a proximal end to a distal end, with the barrel having a single groove formed in an exterior surface of the barrel, with the single groove extending to and forming an opening at the distal end of the barrel;
    deflating an inflatable penile implant to provide a deflated penile implant;
    inserting a first lateral edge of the deflated penile implant into the single groove and inserting a second lateral edge of the deflated penile implant into the single groove;
    placing the barrel of the tool and the deflated penile implant into a corpora cavernosum of a penis;
    sliding the barrel of the tool relative to the deflated penile implant, removing the barrel from the corpora cavernosum of the penis by sliding the first lateral edge of the deflated penile implant and the second lateral edge of the deflated penile implant out of the single groove thus leaving the deflated penile implant in the corpora cavernosum of the penis.

13. The method of claim 12, further comprising:
    clamping a flexible lip associated with the single groove against the first lateral edge of the deflated penile implant and against the second lateral edge of the deflated penile implant.

* * * * *